(12) United States Patent
Jevnikar et al.

(10) Patent No.: US 6,338,850 B1
(45) Date of Patent: *Jan. 15, 2002

(54) METHODS AND PRODUCTS FOR CONTROLLING THE IMMUNE RESPONSE OF A MAMMAL TO GLUTAMIC ACID DECARBOXYLASE

(75) Inventors: Anthony M. Jevnikar; Shengwu Ma; Calvin R. Stiller, all of London (CA)

(73) Assignee: London Health Sciences Centre, Ontario (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/617,874

(22) PCT Filed: Sep. 21, 1994

(86) PCT No.: PCT/CA94/00530

§ 371 Date: May 21, 1996

§ 102(e) Date: May 21, 1996

(87) PCT Pub. No.: WO95/08347

PCT Pub. Date: Mar. 30, 1995

(30) Foreign Application Priority Data

Sep. 21, 1993 (GB) ................................. 9319429

(51) Int. Cl.[7] .......................... A61K 39/00; A01H 5/00; C12N 5/04; C12N 15/12
(52) U.S. Cl. .................... 424/185.1; 435/410; 435/411; 435/412; 435/414; 435/417; 530/350; 800/700; 800/288; 800/306; 800/317.2; 800/317.3; 800/317.4
(58) Field of Search ........................ 530/350; 424/185.1; 800/200, 288, 306, 317.2, 317.3, 317.4; 435/410, 411, 412, 417, 414

(56) References Cited

U.S. PATENT DOCUMENTS

| 5,475,086 A | * | 12/1995 | Tobin et al. |
| 5,484,710 A | * | 1/1996 | Lam et al. |
| 5,643,868 A | * | 7/1997 | Weiner et al. |
| 5,792,620 A | * | 8/1998 | Lernmark et al. |

FOREIGN PATENT DOCUMENTS

| WO | WO88/10120 | 12/1988 |
| WO | WO90/01551 | 2/1990 |
| WO | WO91/06320 | 5/1991 |
| WO | WO91/12816 | 9/1991 |
| WO | WO92/05446 | 4/1992 |
| WO | WO92/06708 | 4/1992 |
| WO | WO92/07581 | 5/1992 |
| WO | WO94/20135 | 9/1994 |

OTHER PUBLICATIONS

Carrinstan et al. J. Virology 64: 1590, 1990.*
Nihala et al. Eur. S. Immunol. 26: 1736. 1994.*
Lamb et al. Immunology 85:447, 1995.*
McFarland et al. Science 274: 2037, 1996.*
Zhang et al. PNAS 88: 10253, 1991.*
Ma et al., Nature Medicine, 3(7):793–796 (1997).
Kay et al., (1989), Immunology, vol. 66, pp. 416–421.
Peng et al., (1990), Clin. Exp. Immunol., vol. 81, pp. 510–515.
Lamont et al., (1989), Imunology, vol. 66, pp. 595–599.
Thompson et al., (1990) Imunology, vol. 11, pp. 396–399.
Weiner et al., (1993), Science, vol. 259, pp. 1321–1324.
Sayegh et al., (1992), Proc. Natl. Acad. Sci. USA, vol. 89, pp. 7762–7766.
Sayegh et al., (1991), JASN, v. 2, p. 787, Abstract 57P.
Hancock et al., (1991), JASN, v. 2, p. 782, Abstract 8P.
Trudel et al., (1992), Plant Science, v. 87, pp. 55–67.
Düring et al., (1990), Plant Molecular Biology, v. 15, pp. 281–293.
Swain, W.F. (1991), Tibtech, v. 9, pp. 107–109.
Mason et al., (1992), Proc. Natl. Acad. Sci. USA, vol. 89, pp. 11745–11749.
Zambryski (1988), Ann. Rev. Genet., vol. 22, p. 1.
Horsch et al., (1985), Science, v. 227, pp. 1229–1231.
Harrison, L.C. (1992), Immunol. Today, 13:348.
Tisch et al., (1993), Nature, 336:72.
Datla et al., (1991), Gene, vol. 101, pp. 239–246.
Sijmons et al., (1990), Biotechnology, v. 8, pp. 217–221.
Lider et al., (1989), J. Immunol., v. 142, pp. 748–752.
Brod et al., (1991), Ann. neurol., v. 29, p. 615–622.
Hiatt et al., (1992), Genet. Eng. NY, v. 14, pp. 49–64.
De Neve et al., (1993), Transgenic. Res., v. 2, pp. 227–237.

* cited by examiner

*Primary Examiner*—Christina Y. Chan
*Assistant Examiner*—Gerald R. Ewoldt
(74) *Attorney, Agent, or Firm*—Burns, Doane, Swecker & Mathis, L.L.P.

(57) ABSTRACT

A method is provided for expressing a mammalian antigen in transformed plants to provide a source of plant material for oral or enteral administration to a mammal to produce tolerance to the antigen.

17 Claims, 13 Drawing Sheets

1  2  3  4

← 1.25 kb

← 1.4 kb

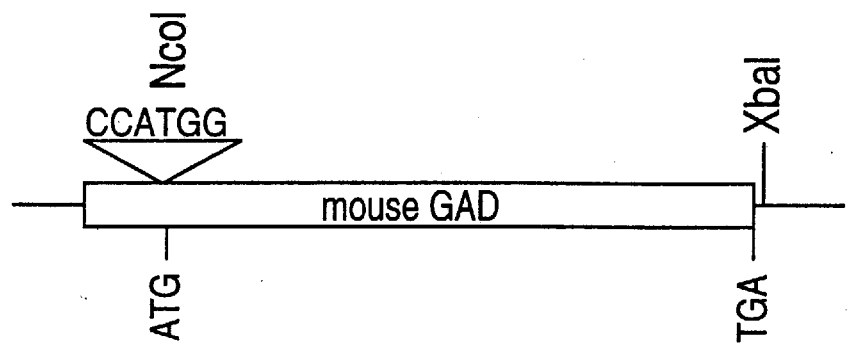
FIG. 12.A.
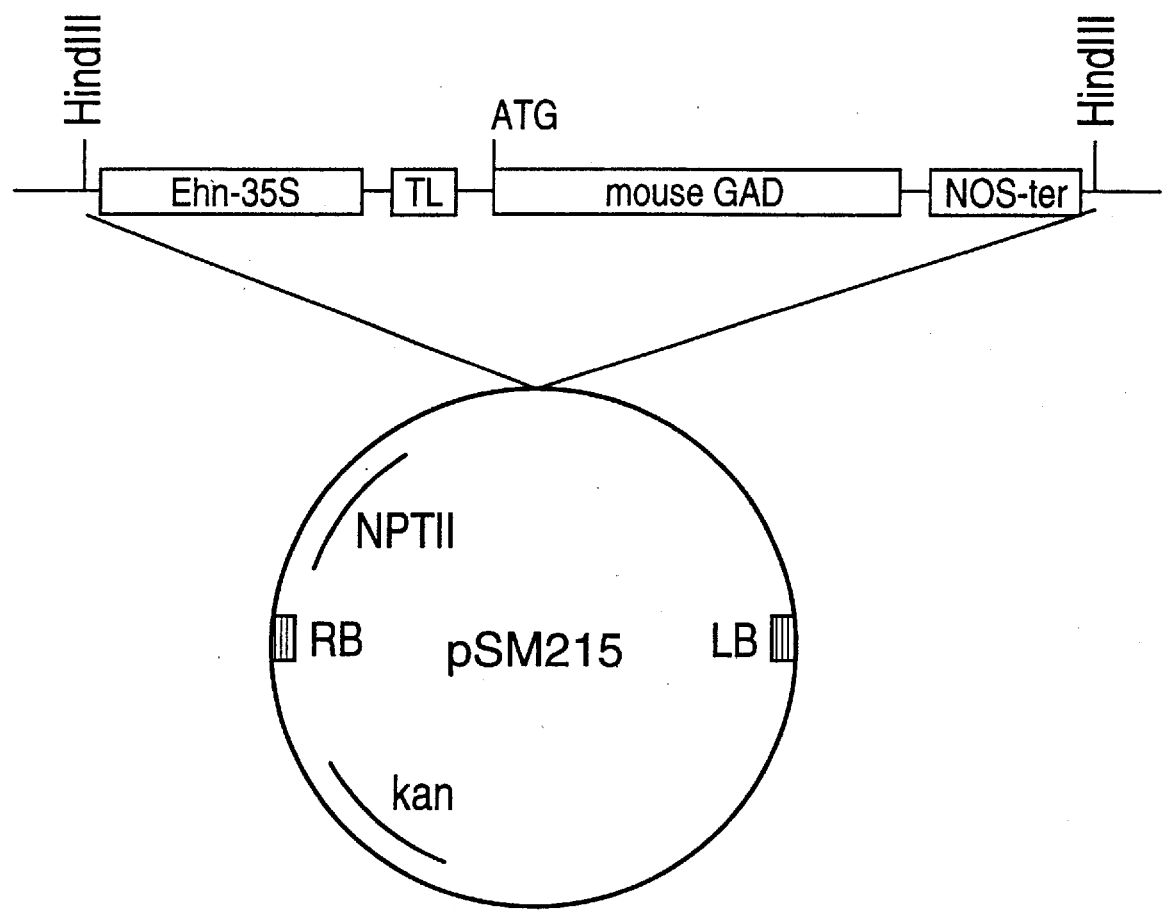
FIG. 12.B.

METHODS AND PRODUCTS FOR CONTROLLING THE IMMUNE RESPONSE OF A MAMMAL TO GLUTAMIC ACID DECARBOXYLASE

This application is a national stage filing under 35 U.S.C. §371 of International Application No. PCT/CA94/00530, filed on Sep. 21, 1994, which International Application was published by the International Bureau in English on Mar. 30, 1995. This application also claims benefit of foreign priority under 35 U.S.C. §119 and/or 35 U.S.C. §365 to Application No. 9319429.8 filed in Great Britain on Sep. 21, 1993; the entire content of which is hereby incorporated by reference.

This invention relates to the production of transgenic plants expressing mammalian proteins which function as antigens.

It further relates to methods for suppressing or reducing the immune response of a mammal to an antigen by oral administration of plants expressing mammalian proteins which function as antigens or parts or derivatives of such plants.

BACKGROUND OF THE INVENTION

Systemic immunosuppressive therapy in autoimmune disease and transplantation is associated with increased rates of infection, malignancy and numerous side effects. The induction of antigen-specific hyporesponsiveness without drugs would therefore be desirable. Immune responses to orally administered proteins are intrinsically modulated and may induce a state of systemic hyporesponsiveness termed oral tolerance (Kay et al., (1989), Immunology, vol.66, pp. 416–421; Peng et al., (1990), Clin. exp. Immunol., vol. 81, pp. 510–515; Lamont et al., (1989), Immunology, vol. 66, pp. 595–599). Although many factors have been implicated in this phenomenon, including soluble mediators and suppressor T cells, it is apparent that antigen processing by mucosal tissue is critical for this effect.

Various studies have been reported of oral administration of antigens thought to be associated with autoimmune diseases, in an effort to induce oral tolerance and prevent or reduce the autoimmune disease.

Oral tolerance to autoantigens has been shown to attenuate experimental induced allergic encephalitis (EAE), adjuvant arthritis (AA), collagen-induced arthritis (CIA) and experimental autoimmune uveoarthritis (EAU) (reviewed in Thompson et al., (1990), Immunology Today, vol. 11, pp. 396–399). The ingestion of myelin basic protein (MBP) during EAE disease has altered its severity, and in recent clinical trials of patients with multiple sclerosis, patients who received MBP had fewer clinical exacerbations during the study period and had reduced numbers of MPB reactive T cells in peripheral blood (Weiner et al., (1993), Science, vol. 259, pp. 1321–1324).

In International Patent Application Publication No. WO 92/07581, and in Weiner et al. (1992), Proc. Natl. Acad. Sci. USA, vol. 89, pp. 7762–7766, Weiner et al. describe suppression of the mammalian response to allografts by oral administration of splenocytes or splenocyte preparations from tissue donors or of short synthesised peptides corresponding to fragments of class II Major Histocompatibility Complex (MHC) proteins.

There are, however, several problems associated with this approach. Firstly, the complexity of foreign peptide presentation in transplantation makes it difficult to screen peptide sequences suitable for induction of tolerance.

Secondly, the induction of oral tolerance to antigens is dose dependent and insufficient oral antigen may prime gut lymphocytes and cause the opposite and undesired effect of sensitisation. It is therefore necessary to be able to obtain the antigens in large quantities.

Thirdly, the nature of the peptide itself may cause increased rather than reduced immune responsiveness.

If whole antigen proteins are used to induce oral tolerance, there is a greater array of potentially tolerance-inducing peptides presented to the immune system. If complex antigens such as MHC proteins or other transplantation antigens are to be used as intact proteins, however, it is difficult to obtain these proteins in sufficient quantities by in vitro synthesis.

The approach of the present invention to overcoming these problems, not suggested by any of the previously mentioned references, is the expression of appropriate mammalian antigens, for example transplantation antigens or autoantigens, in plants and the administration of these plants or plant materials derived from these plants to a mammal to produce oral tolerance to the expressed mammalian antigens in order to control or suppress allograft rejection or autoimmune responses in the mammal.

Transgenic plants have been used to express a variety of single chain heterologous polypeptides with considerable success (Trudel et al., (1992), Plant Science, v. 87, pp. 55–67). More complex multi-chain proteins such as antibodies have been expressed with less consistent results (Swain, W. F. (1991), Tibtech, v. 9, p. 107).

It has been proposed to express viral antigens in plants with the hope of providing an "edible vaccine", whereby ingestion of plants containing the viral antigen by a human would stimulate an increased immune response and provide immunisation against the virus (Mason et al., (1992), Proc. Natl. Acad. Sci. USA, vol. 89, pp. 11745–11749).

No previous references propose the reduction or suppression of the immune response of a mammal by the administration to the mammal of plants or plant material expressing an appropriate mammalian antigen.

SUMMARY OF THE INVENTION

In accordance with one embodiment of the invention, novel plasmids have been constructed for introduction of DNA sequences encoding mammalian antigens such as transplantation antigens or autoantigens into suitable plants.

In accordance with a further embodiment of the invention, novel transgenic plants are provided having inserted into their genome DNA sequences encoding mammalian antigens such as transplantation antigens or autoantigens, these plants being able to express the inserted DNA sequences and produce the antigens encoded therein.

In accordance with a further embodiment of the invention, a method is provided for suppressing or reducing the immune response of a mammal to an antigen, comprising administering orally or enterally to the mammal an effective dose of plant tissue containing an effective amount of the antigen, the plant tissue being obtained from a transgenic plant having in its genome a heterologous expressible gene for the antigen.

In accordance with a preferred embodiment of the invention, a method is provided for controlling or suppressing an immune response of a mammal to an allograft comprising administering orally or enterally to the mammal an effective amount of plant tissue in which is expressed at least one transplantation antigen specific to the allograft whereby the immune response to the allograft is controlled or suppressed.

In accordance with a further preferred embodiment of the invention, a method is provided for controlling or suppressing an autoimmune response of a mammal to an autoantigen comprising administering orally or enterally to the mammal an effective amount of plant tissue in which is expressed the autoantigen whereby the autoimmune response is controlled or suppressed.

SUMMARY OF DRAWINGS

Certain embodiments of the invention are described, reference being made to the accompanying drawings, wherein.

SS=murine signal sequence

TM=transmembrane sequence

CYTO=cytoplasmic tail

SS=barley α-amylase signal sequence

Figure 3:
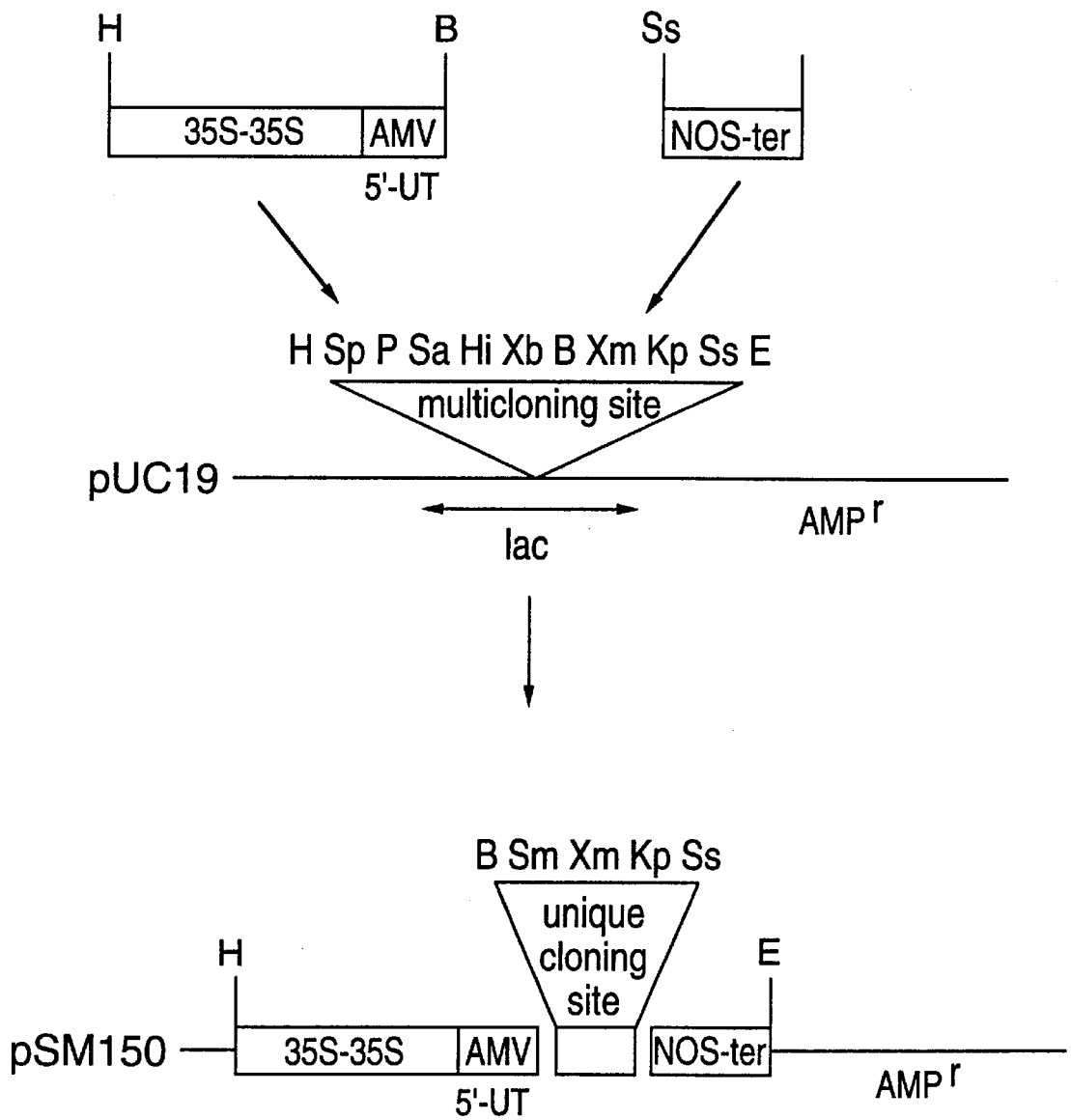

FIG. 3 shows in schematic form the construction of plasmid pSM150. The plasmid is shown in linear form.

Figure 4:
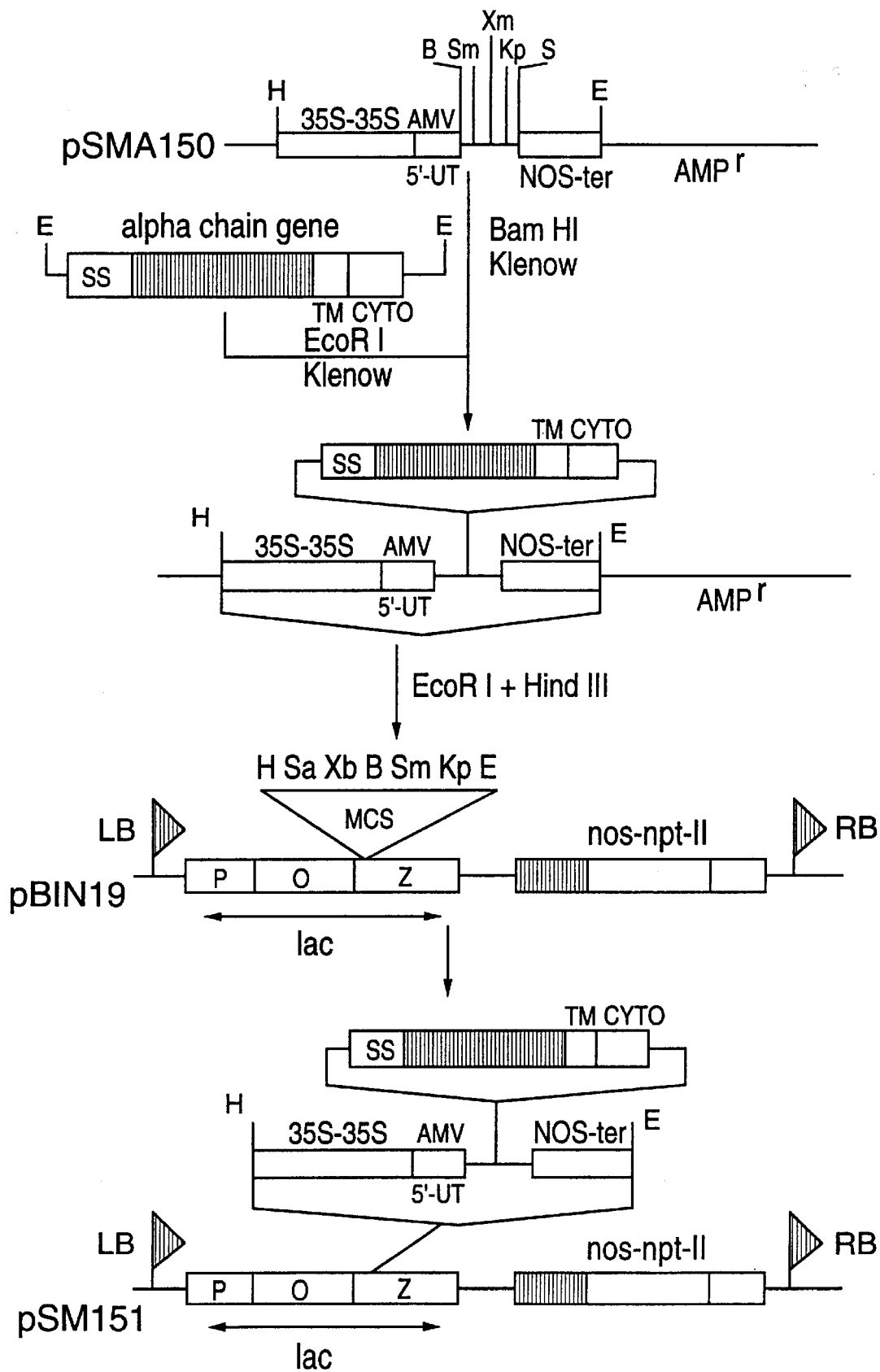

FIG. 4 shows in schematic form the construction of plasmid pSM151.

Figure 5:
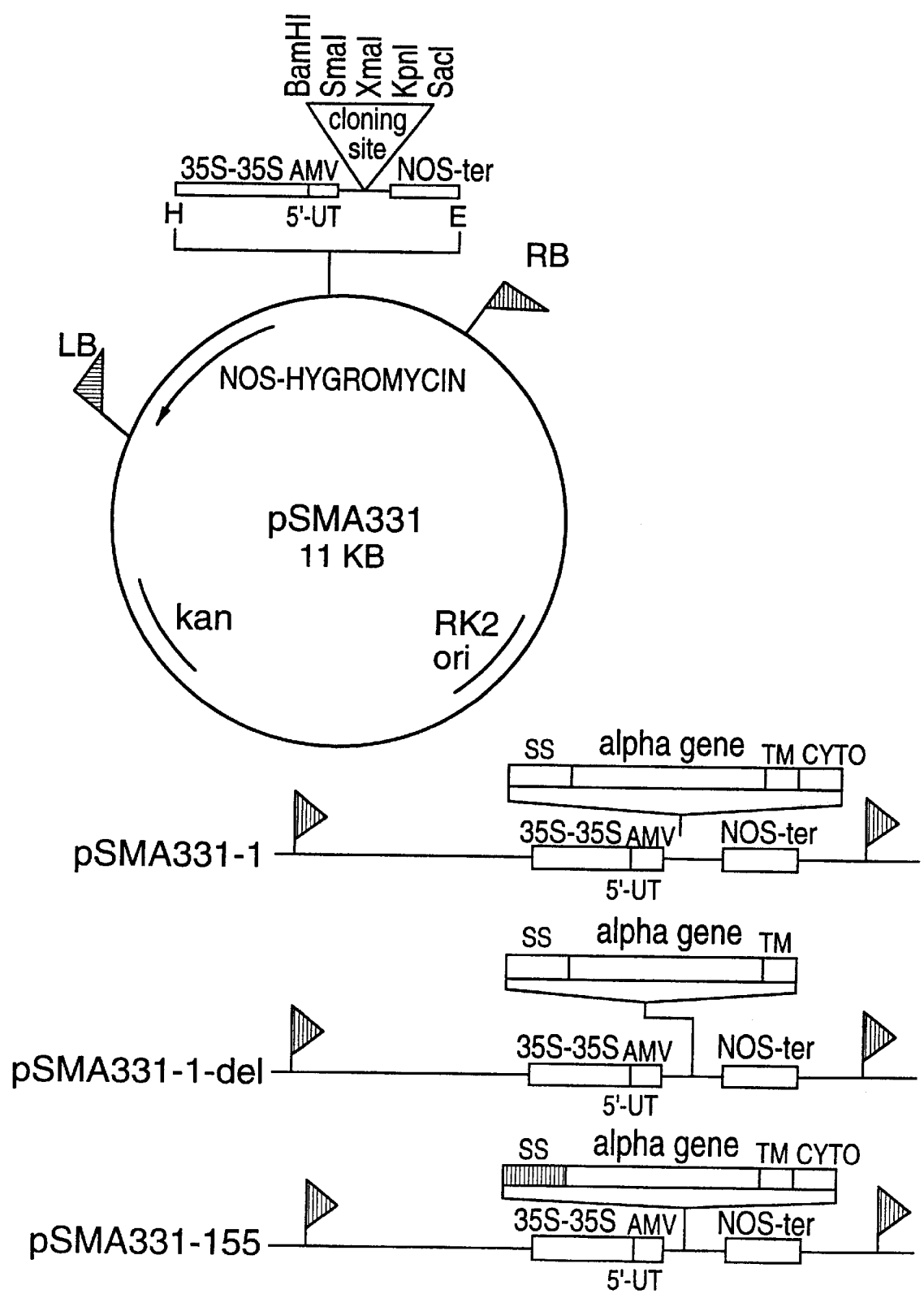

FIG. 5 shows in schematic form the construction of plasmid pSMA331 and derivatives.

Figure 6:
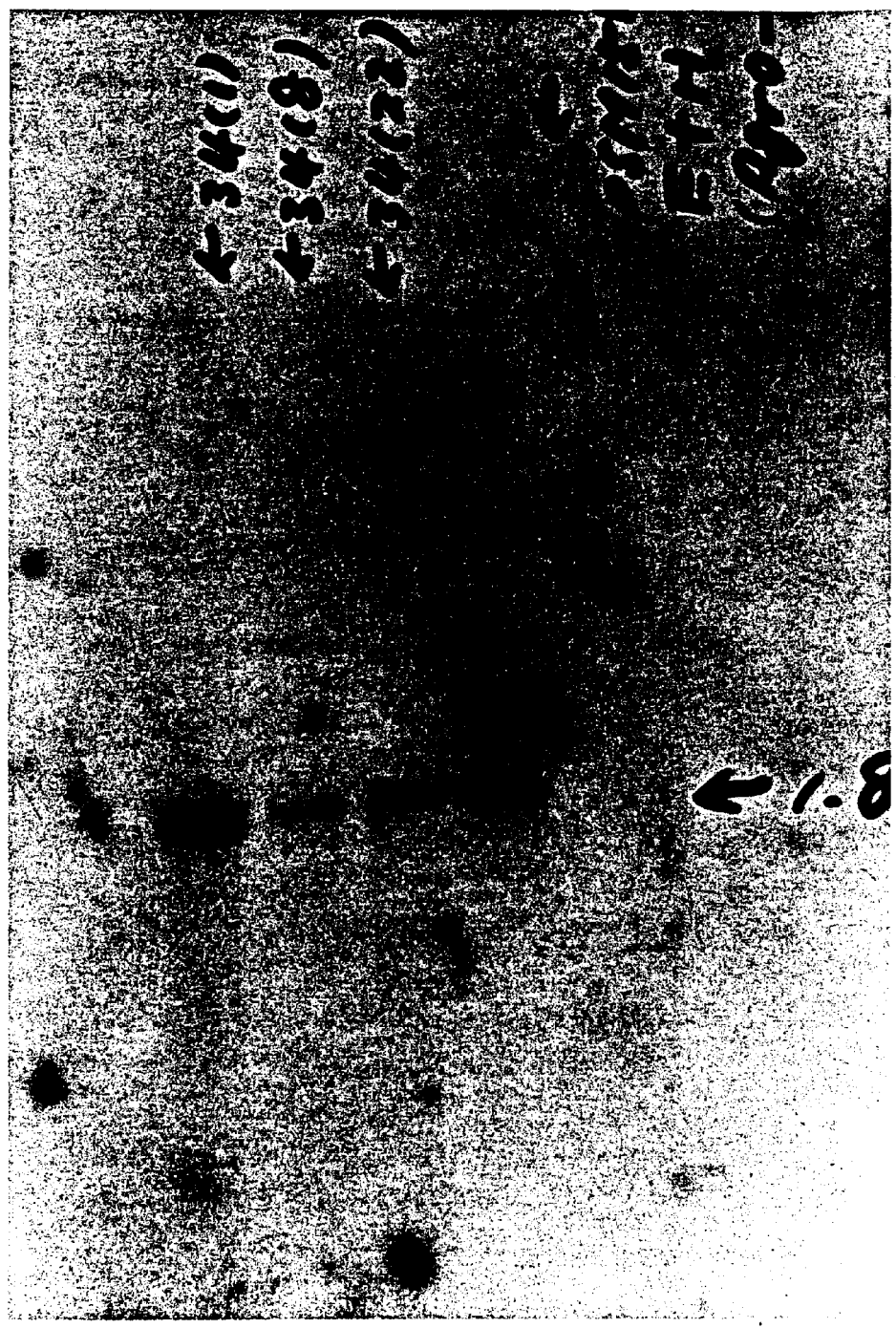

FIG. 6 shows Southern blot of DNA fragments from plants bearing murine MHC α chain transgene:

Lane 4: Control: 1.8 kb DNA fragment excised from plasmid pSM151 with EcoR1/Hind III.

Lanes 1 to 3: α chain DNA from three representative transformed tobacco plants.

Figure 7:
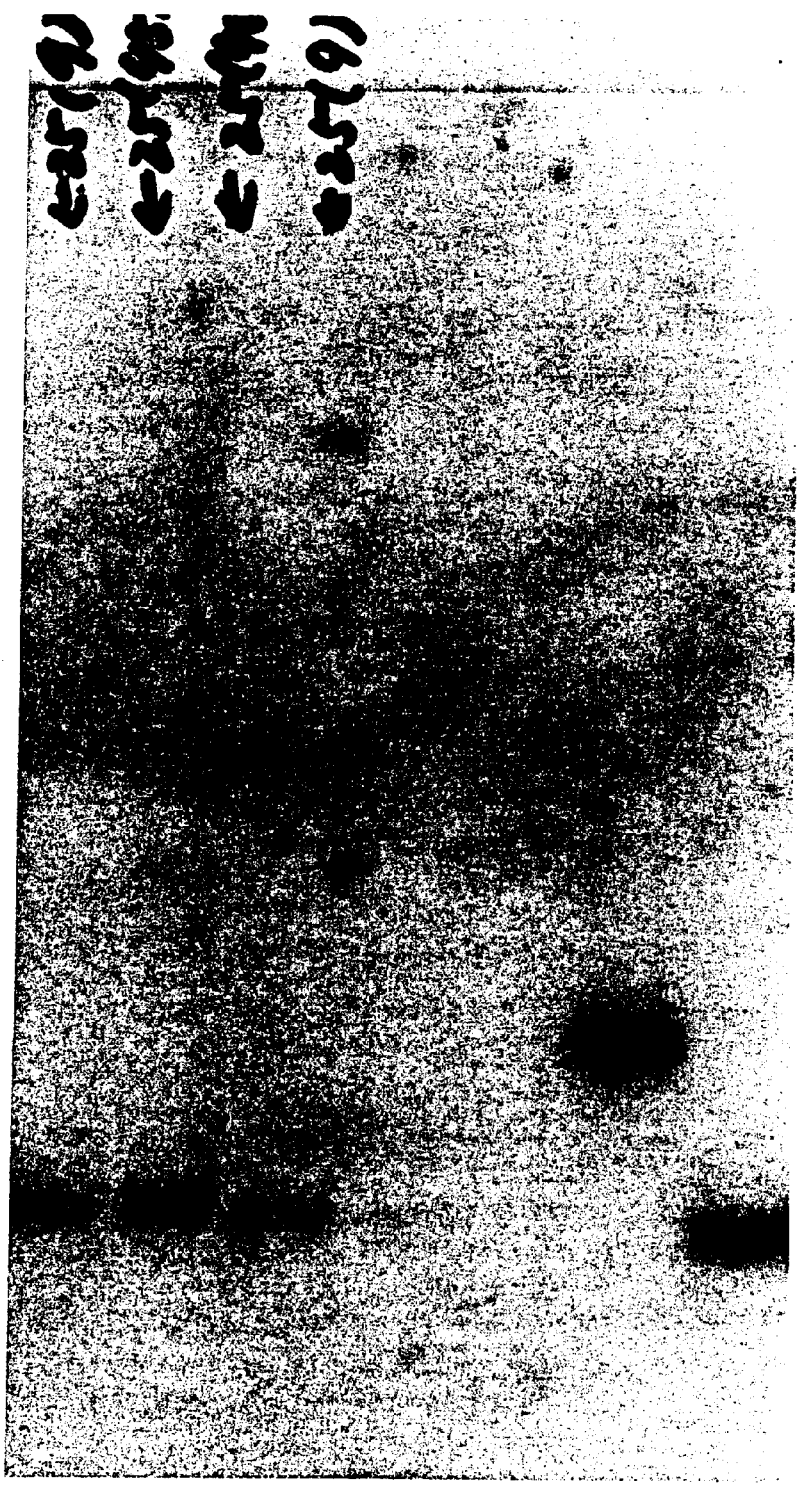

FIG. 7 shows Southern blot of DNA fragments from plants bearing murine MHC β chain transgene:

Lane 6: Control: 1.8 kb DNA fragment excised from plasmid pSM152 with EcoR1/Hind III.

Lanes 1 to 4: β chain DNA from four representative transformed tobacco plants.

Lane 5: DNA fragment with larger size, likely due to incomplete digestion.

Figure 8:
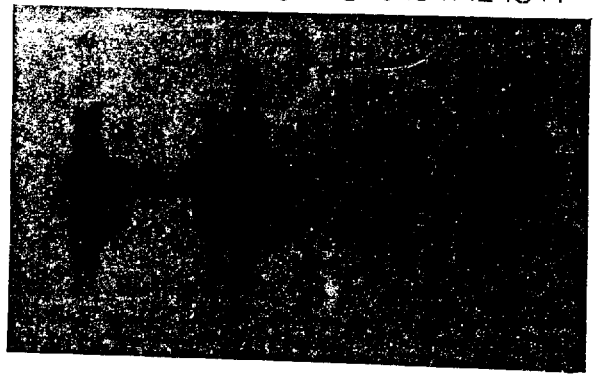

FIG. 8 shows Northern blot analysis of α chain gene transformants.

Lane C: mouse spleen cell positive control RNA;

Lanes 1 to 14: individual transgenic lines transformed with α chain plasmid. Arrow indicates the 1.25 kb chimaeric α gene transcript.

Figure 9:

FIG. 9 shows Northern blot analysis of β chain gene transformants.

Lane C: mouse spleen cell positive control RNA; C, RNA extracted from mouse spleen cells; Lanes 1 to 16 individual transgenic lines transformed with β chain plasmid. Arrow indicates the 1.4 kb chimaeric β gene transcript.

Figure 10:
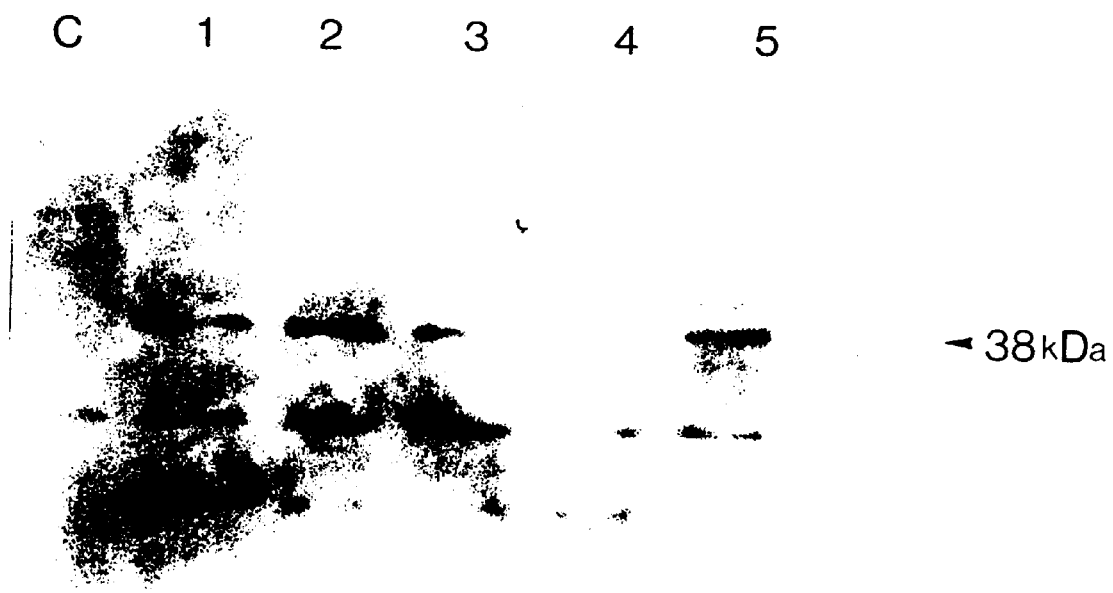

FIG. 10 shows Western blot analysis of α chain gene transformants.

Lane C: untransformed control plants; Lanes 1 to 5 extracts from individual transgenic lines. Arrow indicates the expected size of the 38 kDa α chain polypeptide. Additional bands are non-specific.

Figure 11:
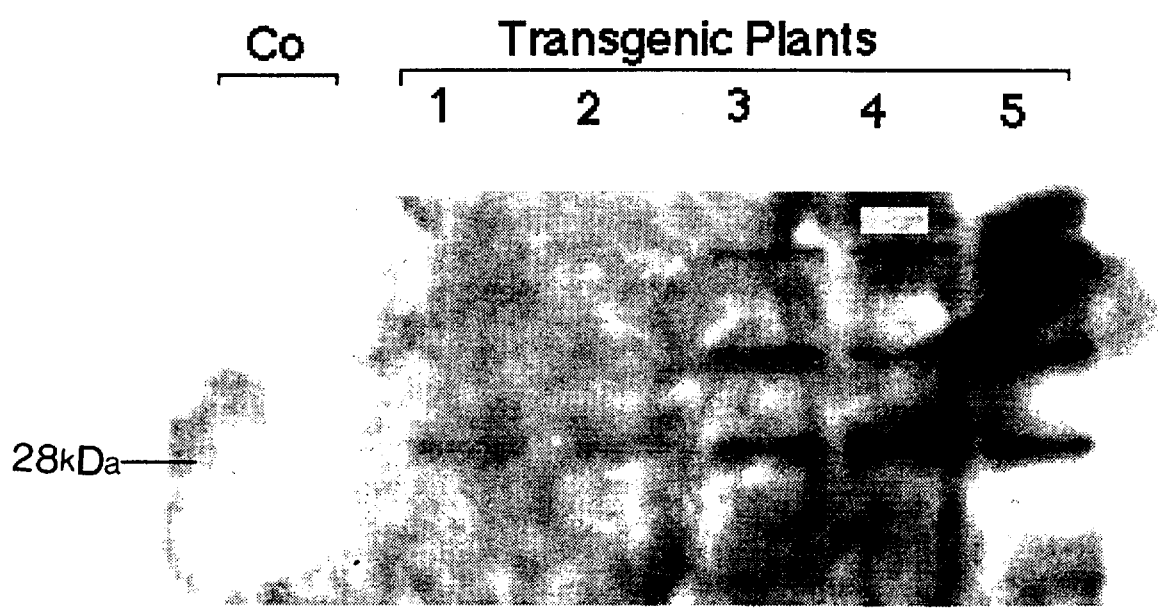

FIG. 11 shows Western blot analysis of β chain gene transformants.

Lanes C: untransformed control plants; Lanes 1 to 5: extracts from individual transgenic lines. Arrow indicates the expected size of the 28 kDa β chain polypeptide. Additional bands are non-specific.

FIGS. 12A and 12B show in schematic form the construction of plasmid pSM215.

FIG. 12A shows a map of mouse GAD65 cDNA.

FIG. 12B shows a map of expression vector pSM215.

Figure 13:
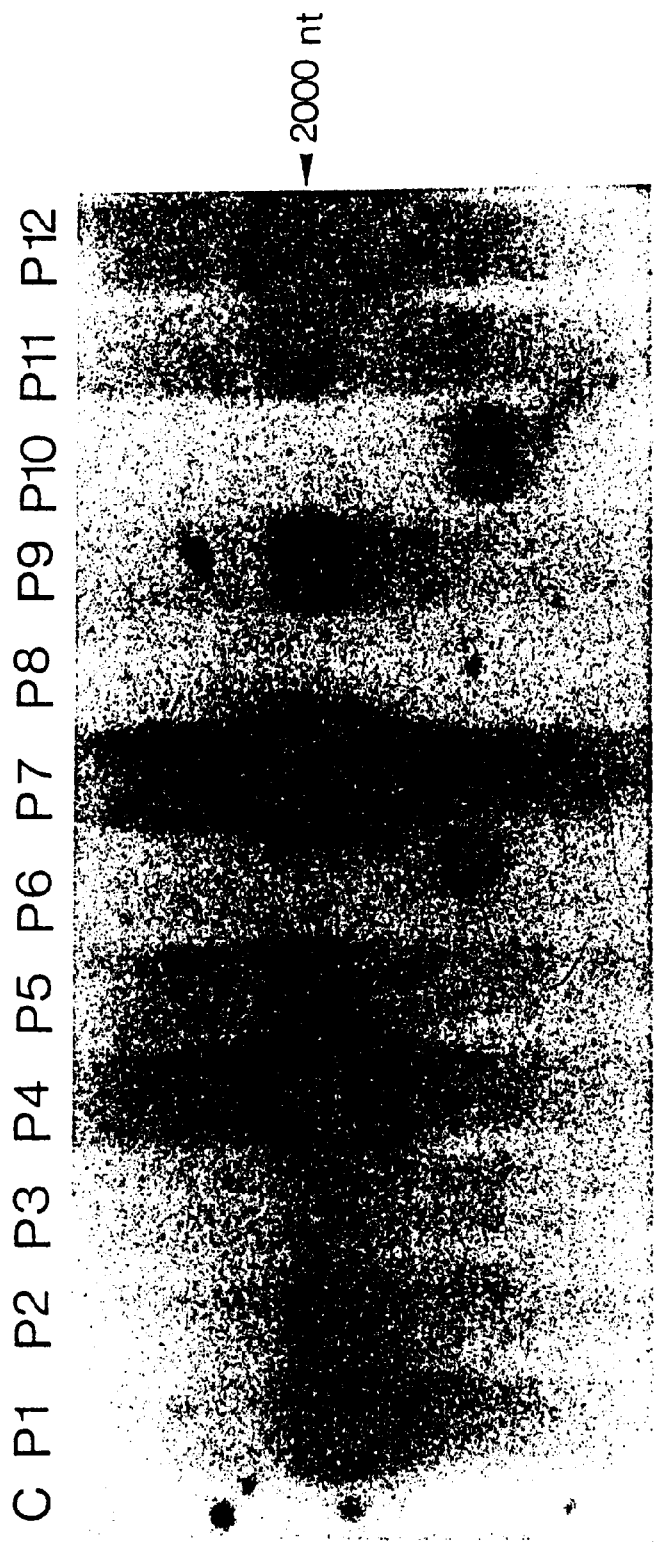

FIG. 13 shows a Northern blot analysis of murine GAD expression in transgenic tobacco plants. Total RNA was extracted from transgenic leaves and 25 μg loaded on a gel. After blotting, the membrane was hybridized with $^{32}$P-labelled GAD cDNA Lane C: untransformed control plants. Lanes P1–P12: individual transgenic lines selected after transformation with pSM 215. The arrow indicates the 2.0 kb chimaeric GAD mRNA transcript size.

Figure 14:
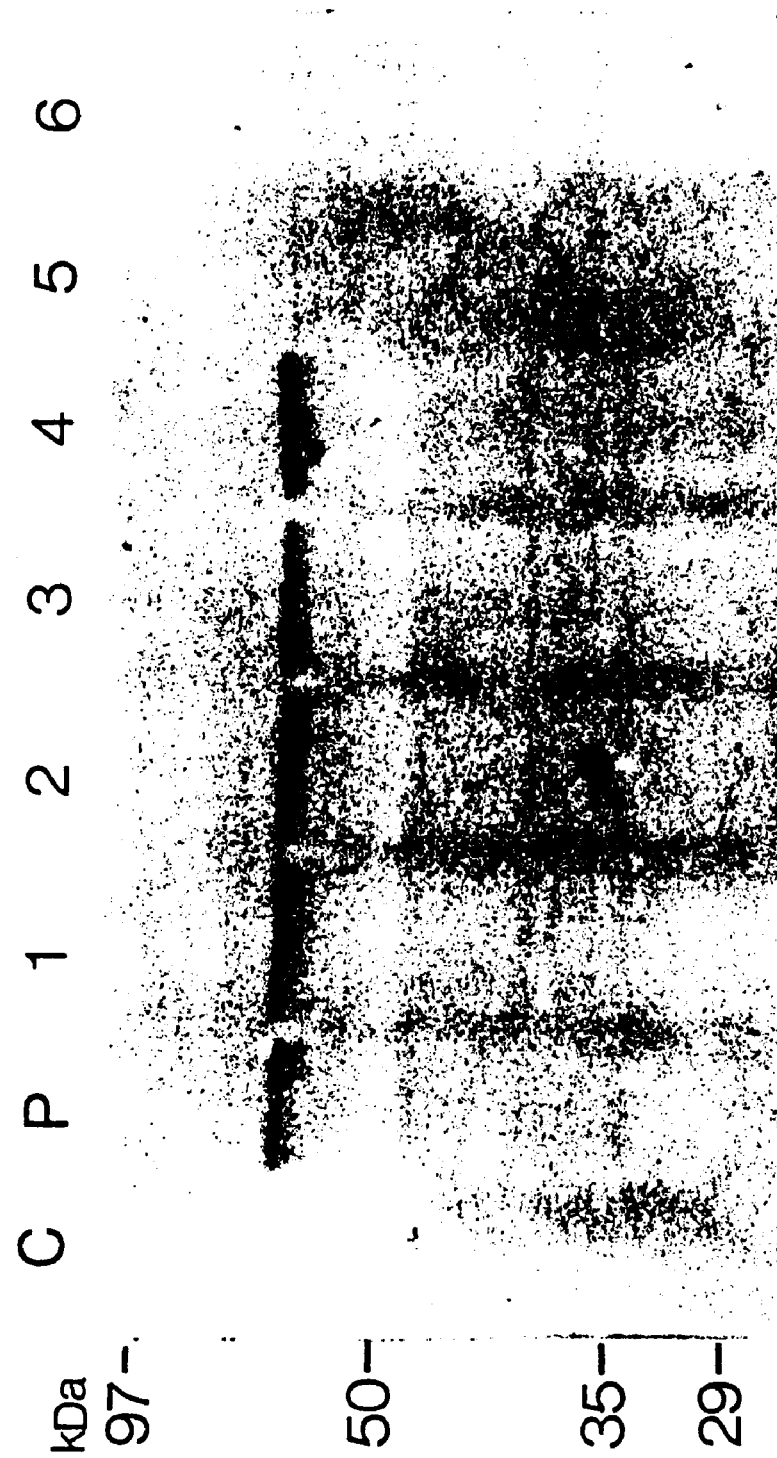

FIG. 14 shows a Western blot of murine GAD expression in transformants.

Lane C: untransformed control plants; Lane P: purified mouse GAD (100 ng); Lane 1: extracts from transgenic line P1; Lane 2: extracts from transgenic line 2; Lane 3: extracts from transgenic line 4; Lane 4: extracts from transgenic line 7; Lane 5: extracts from transgenic line 9; Lane 6: extraction from transgenic line 12. Protein size standards are indicated on the left side of the figure.

Figure 15:
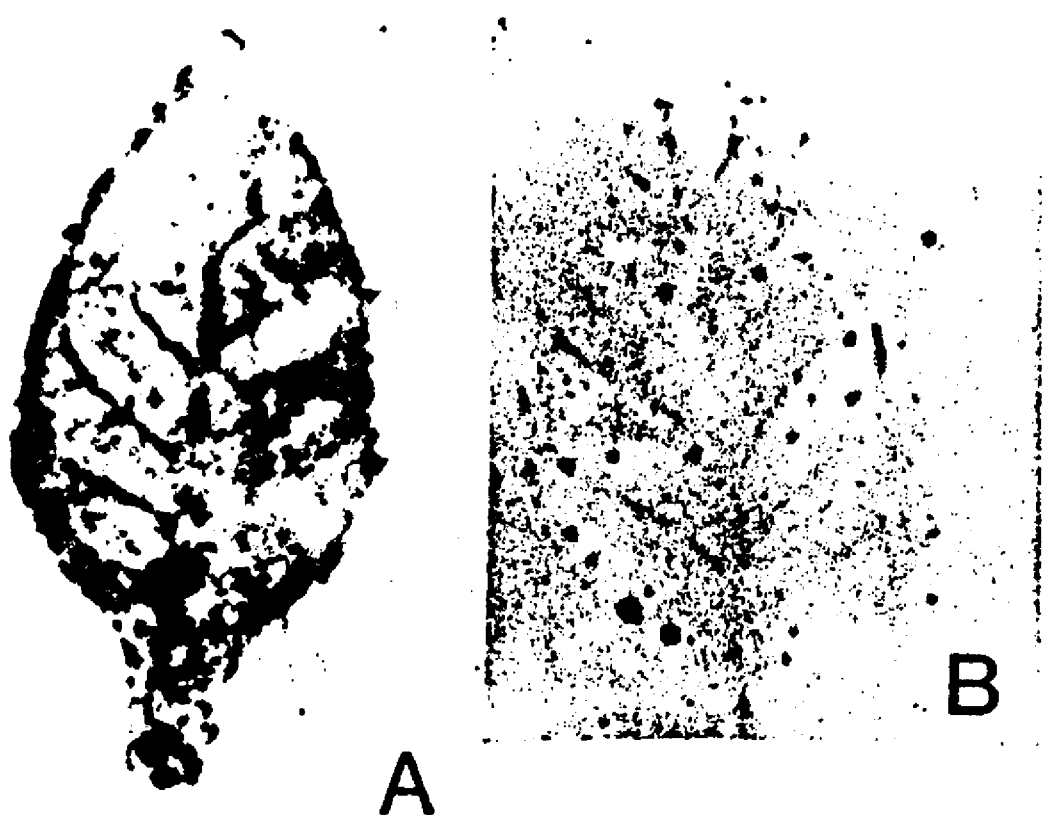

FIG. 15 shows a tissue print of A: a transgenic tobacco leaf and B: a control untransformed leaf probed with an anti-GAD antibody and chemoluminescent second antibody.

DETAILED DESCRIPTION OF INVENTION

The present invention provides for producing immune-response provoking proteins or polypeptides in quantities suitable for the induction of oral tolerance in mammals, including humans, by transforming plants to produce the desired proteins or polypeptides or immunosuppressive, tolerance inducing fragments or derivatives of these proteins or polypeptides. Examples of such immune response-provoking proteins include transplantation antigens which provoke a response against engrafted tissue, leading to graft rejection, and autoantigens which provoke an immune response against a mammal's own tissues, leading to autoimmune diseases.

The invention also provides a new method for inducing tolerance in a mammal to a selected immune response-provoking protein or polypeptide by administering orally or enterally to the mammal plant material derived from plants transformed so as to express the selected protein or polypeptide or immunosuppressive fragments or derivatives thereof in their tissues.

Plant materials for oral or enteral administration in accordance with the invention include plant tissue or plant parts containing the desired protein, for example leaves, tubers etc. and preparations or extracts of proteins derived from such plants. Plant parts may be consumed raw or after minimal culinary preparation. Plant preparations or extracts may comprise total plant protein or purified or partially purified preparations of the transgenic protein of interest.

An "immunosuppressive fragment" of an immune response-provoking protein or polypeptide means a portion of the amino acid sequence of the protein or polypeptide which is capable, on oral or enteral administration to a mammal, of inducing tolerance or suppressing the immune response of the mammal to the protein or polypeptide.

An "immunosuppressive derivative" of an immune response-provoking protein or polypeptide means an analogue thereof which retains the ability, on oral or enteral administration to a mammal, of inducing tolerance or suppressing the immune response of the mammal to the protein or polypeptide.

Foreign antigen is recognized by mammalian T cells only following digestion into small fragments, binding of the fragments to Major Histocompatibility Complex (MHC) molecules within the cell and surface presentation by specialized antigen presenting cells (APC)(Hamilos, D. L., (1989), *cell. Immunol.*, 8, 98–117; Schwartz, R. H., (1990), *Science*, 248, 1349–1356). The recognition of this bimolecular complex (antigen-MHC) on the surface of APC leads to activation of T cells. The recognition of class II MHC molecules by CD4+T cells results in proliferation, while in contrast, CD8+T cells cause target cell death on encountering antigen-class I complex bearing cells. The selectivity of this interaction is determined by CD4 and CD8 accessory molecules which engage specific regions of the MHC molecules (Robey, E. et al., (1991), *Proc. Natl. Acad. Sci. USA*, 88, 608–612).

Major histocompatibility complex (MHC) Class II molecules are integral transmembrane proteins encoded by polymorphic genes of the MHC and are members of the immunoglobulin gene superfamily. They consist of two chains, $\alpha$(34–38 kDa) and $\beta$(26–28 kDa), each of which contains two external domains anchored to the cell surface by a transmembrane spanning region and a short intracytoplasmic tail (Germain, R. N. et al., (1986), *Ann. Rev. Immunol.*, 4, 281–315). Both in man and in mice, the $\alpha$ chain is essentially non-polymorphic and there is little variation in sequences among the $\alpha$ chain families (Estess, P. et al., (1986), *Proc. Natl. Acad. Sci. USA*, 83, 3594–3598). In contrast, the $\beta$ chains are highly polymorphic, and largely determine the identity of associated heterodimers.

Although the antigen specificities of allograft rejection are incompletely understood, the participation of MHC class II molecules in most cell mediated immune responses is clear, and targeting of class II molecules by monoclonal antibodies has been found to attenuate transplant rejection.

For control or suppression of transplant rejection in mammals, including humans, transplantation antigens such as the MHC class I or class II proteins therefore are suitable agents for induction of oral tolerance.

The methods of the invention permit the setting up of a bank of transformed plants each capable of expressing a different human MHC protein or sub-unit chain. For example, for the DR, DQ and DP regions of the class II human MHC proteins, a bank of about twenty to thirty types of transgenic plants could be set up. From such a bank of material, one would then select a desired transplantation antigen to which one wished to induce tolerance.

For class I human MHC proteins, a larger bank of transformants, possibly 60 or 70 types, would be required. Alternatively, plant materials such as extracts may be prepared and stored.

In accordance with one approach to inducing tolerance, a transplant patient would receive self-MHC proteins or immunosuppressive fragments or derivatives thereof.

Alternatively, a transplant patient would receive MHC-proteins or immunosuppressive fragments or derivatives of a type corresponding to the donor tissue.

The choice of transgenic plant material would be related to the MHC expression of the donor tissue, established by tissue typing prior to transplant.

Plant material or purified protein from an appropriately transformed plant containing an effective dose of the desired transplantation antigen, or an immunosuppressive fragment or derivative of the antigen, is administered orally or enterally to the transplant or graft recipient commencing prior to transplantation or grafting and continuing with daily administration thereafter.

Many diseases are considered to be autoimmune in origin and the suspected autoantigen has been identified in a number of cases. Even where the autoantigen has not yet been defined, the participation of MHC class II molecules in the immune response of autoimmune diseases makes these molecules suitable candidates for induction of tolerance in order to ameliorate the disease.

Autoimmune disease can therefore also be controlled or suppressed by induction of tolerance to MHC class II proteins by administration of plant material from suitably transformed plants in accordance with the invention.

Alternatively, where an autoantigen involved in an autoimmune response has been identified, plants may be transformed by the methods of the invention to express that autoantigen or an immunosuppressive fragment or derivative thereof and the disease may be treated by oral or enteral administration of plant material from such transformants to induce tolerance, for example, myelin basic protein for multiple sclerosis, glutamic acid dehydrogenase or an islet cell-specific antigen for diabetes, thyroglobulin for autoimmune thyroiditis or collagen for rheumatoid arthritis.

Treatment would be commenced as soon as the autoimmune disease or a pre-clinical stage thereof was diagnosed.

As autoantigens associated with particular diseases are identified, suitable plant transformants may be prepared by the methods of the invention and either plants or plant materials maintained in readiness for therapeutic administration.

Several putative islet "self" antigens have been identified including islet cell antigen (ICA), glutamic acid decarboxylase (GAD), insulin, heat shock protein, islet granule associated antigen etc., (Harrison, L. C. (1992), *Immunol. Today*, 13: 348). It has been suggested the GAD65 may be the earliest antigen in NOD mice to provoke an immune response (Tisch, R., X.-D. Yang, S. M. Singer, R. S. Liblau, L. Fugger and H. O. McDevitt, (1993), *Nature*, 366: 72), and overt insulitis may be preceded by the appearance of autoantibodies directed against several $\beta$ cell proteins such as GAD, insulin and an islet derived glycoprotein (p69) (Pietropaolo, M. L., L. Castano, S. Babu, et al., (1993), *J. Clin. Invest.* 92: 359). This suggests that GAD may be a relevant autoantigen in diabetes.

The inventors have created novel recombinant vectors for the introduction into and expression of mammalian genes encoding desired antigens in suitable plant hosts.

In accordance with one embodiment of the invention, a cDNA sequence coding for a selected mammalian antigen was inserted into a DNA construct under control of a promoter functional in plant cells (hereafter, unless otherwise specified, "a plant promoter") and in proper reading frame with a transcription termination sequence functional in plant cells, to provide for expression of the mammalian DNA in plant tissue.

As will be understood by those skilled in the art, a variety of plant promoters may be used to express mammalian genes in plants, including promoters derived from plants and promoters derived from plant viruses.

Although mammalian transcription termination sequences do function in plants and may be employed, it is preferable to remove the mammalian 3' untranslated sequence and replace it with a termination sequence such as a plant gene 3' termination sequence, a plant virus gene termination sequence or an Agrobacterium termination sequence.

In accordance with a preferred embodiment of the invention, a recombinant vector is provided in which a cDNA sequence coding for a selected mammalian antigen is inserted under the control of the Cauliflower Mosaic Virus 35S promoter and the nopaline synthase polyadenylation termination sequence. The 35S promoter with double enhancer sequence, Ehn-35S, is especially preferred.

In accordance with a further embodiment of the invention, a vector is provided in which the cDNA sequence under control of the 35S promoter is a cDNA sequence encoding either MHC α chain or MHC β chain.

In accordance with a further embodiment, a vector is provided in which the cDNA sequence under control of the 35S promoter encodes GAD.

In accordance with a further embodiment, the DNA sequence encoding the mammalian signal peptide may be removed from the DNA for the mammalian antigen and replaced by a plant signal sequence as described in Example 2, where the sequence coding for barley α amylase signal peptide was substituted. Other suitable plant signal peptide DNA's will be known to those skilled in the art, for example tobacco pathogen resistance protein (PR protein) signal peptide.

In accordance with a further embodiment, the DNA sequence encoding the mammalian C-terminal cytoplasmic domain was removed before insertion of the cDNA into the plasmid, as in Example 3.

By similar means, genes or cDNA sequences coding for a selected human antigen such as an autoantigen or a transplantation antigen may be introduced into the recombinant vectors of the invention for preparation of transgenic plants expressing these antigens.

The novel vectors of the invention may be used to transform a selected plant by a variety of methods which will be known to those skilled in the art.

In accordance with a preferred embodiment of the invention, a plasmid carrying DNA encoding the desired antigen is transfected into plants and integrated into the plant genome by Agrobacterium-mediated gene transfer, as described by Zambryski (1988), Ann. Rev. Genet., vol. 22, p.1. In a model system using tobacco plants, plasmids in accordance with the invention have been introduced by the leaf disk transformation method of Horsch et al., (1985), Science, v. 227, pp. 1229–1231).

Incorporation of a suitable marker gene in the plasmid used for transfection permits selection of transgenic plants, as is well known to those skilled in the art and illustrated by the examples herein.

Although Agrobacterium-mediated transfer is preferred, other suitable methods of introducing the mammalian antigen DNA into suitable plants will be known to those skilled in the art. Such methods include polyethylene glycol (PEG) mediated gene transfer, calcium phosphate co-precipitation, electroporation, liposome fusion, microinjection and particle bombardment (37,38).

The inventors have successfully introduced the genes for mouse MHC II α and β chain proteins into the genomic DNA of tobacco plants, as described in Example 6.

Although tobacco is not a plant which is likely to be suitable for ingestion, due to the presence of substances such as nicotine and alkaloids, this system indicates that mammalian antigens such as MHC II proteins can be introduced into plant tissue, so providing a means for producing oral tolerance to a desired antigen by oral or enteral administration of a suitable transgenic plant or of plant materials derived from such a plant. As will be understood by those skilled in the art, similar methods may be employed for production of transgenic edible plants producing a desired mammalian antigen, such plants including, for example, tomatoes, alfalfa, and potatoes or of non-toxic, low-alkaloid strains of tobacco. As described in the examples, a vector carrying the gene for mammalian GAD has been transfected into potatoes and transformants have been obtained.

In accordance with a further embodiment of the invention, a cDNA sequence coding for mouse GAD was inserted into an expression vector under control of a plant promoter, as described in Example 7, and used to transform tobacco plants by means of agrobacterium-mediated transfection.

Examination of extracts of total protein from leaf tissue of transfected tobacco plants by Western blotting showed a band of protein hybridising to an anti-GAD antibody probe and of molecular weight identical to control purified mouse GAD. Tissue printing of intact transformed leaves indicated that the heterologous mammalian protein was distributed widely throughout the leaf tissue in a generally uniform fashion, as seen in FIG. 15.

Comparison of Western blot bands obtained with known amounts of purified mouse GAD or from extracts of transformed leaves by scanning densitometry allowed calculation of the yield of mammalian protein in the transformed plants. Mouse GAD protein was calculated to comprise approximately 0.4% of total soluble leaf protein.

This impressive level of expression indicates that a tolerance-producing dose of antigen can be administered to a human patient by the feeding of around 30 gm of leaf material.

Visual examination of the Western blots of expressed MHC class II α chain and β chain from transformants indicate a similar level of transgenic protein production.

In accordance with a further embodiment of the invention, a cDNA coding for human GAD has been inserted into an expression vector and used to create transgenic potato plants by means of agrobacterium-mediated transfection, as described in Example 8.

Transgenic starch tubers provide a very inexpensive source of biomass for heterologous protein production.

Transgenic plants expressing the desired antigen may be identified by examination of plant extracts by Western blotting, by conventional techniques, expressed antigen being detected by means of an appropriate specific antibody, as further described in the Examples.

Where the antigen to which tolerance is desired has a heterodimeric structure, as for human or murine MHC II proteins, one may either transform plant tissue sequentially with two vectors, each carrying the DNA for an individual protein chain and a different selection in marker gene, as described in Example 6, so that the plant produces the mature antigen, or one may introduce the DNA for each chain into separate plants and breed these, by cross-pollination of "single chain" plants by standard techniques to give hybrids producing the mature antigen.

In order to produce oral tolerance in a subject to a particular mammalian antigen, transgenic plant tissue containing the expressed antigen may be administered orally or enterally to the subject in an effective dose.

Alternatively, if a non-edible transgenic plant is used for production of mammalian antigens, the antigens may be extracted from the plant tissue and purified as required by standard methods before oral or enteral administration.

EXAMPLE 1

Novel plasmids have been created for introduction of MHC genes into plants. All vectors constructed share the 35S-35S promoter, multiple cloning site and nopaline synthase polyadenylation termination sequences. Two independent selectable markers, kanamycin and hygromycin, have been used.

CONSTRUCTION OF pSM150

A 650 bp HindIII and BamHI fragment derived from plasmid pBI4104 was provided by Dr. R. S. Datla, Plant Biotechnology Institute, NRC Canada, Saskatoon. (Datla et al., (1991), Gene, v. 101, pp. 239–246; Hobbs et al., (1990), Plant Cell Reports, v. 9, pp. 17–20). The fragment contained the Cauliflower Mosaic Virus (CaMV) 35S promoter with a duplicate enhancer sequence followed by the 5' untranslated Alfalfa Mosaic Virus (AlMV) RNA4 leader sequence, was cloned into the polylinker of pUC19.

To make a complete expression cassette, a 260 bp SstI and EcoR1 fragment representing the polyadenylation signal of nopaline synthase was also ligated to the polylinker of pUC19. The remaining restriction sites flanked by 35S-dual enhancer and 3'-nos and suitable for cloning, include BamHI, SmaI, AvaI, KpnI and SacI. pSM150 was used as the initial plant expression vector for the construction of chimeric mouse class II MHC I-A $\alpha$ and $\beta$ genes. Construction of the plasmid is shown schematically in FIG. 3.

CONSTRUCTION OF pSM151

The full length cDNA sequence for murine class II MHC I-A $\alpha$ gene subunit was obtained from Dr. Laurie Glimcher, The Harvard School of Public Health; this cDNA encodes molecules of 1-A$\alpha^k$ haplotype.

Figure 1:
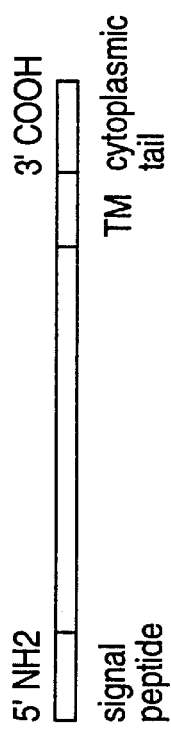
FIG. 1 shows the general scheme of native murine MHC class II α or β cDNA. TM=transmembrane sequence.

The cDNA, as schematically represented in FIG. 1, encodes the mature protein with intact leader peptide, transmembrane spanning portion and cytoplasmic tail. In the $\alpha$ chain, the leader peptide is encoded by 69 base pairs. The full length cDNA sequence was isolated as a single EcoR1 fragment with the size of about 1.1 kb. After treatment with klenow enzyme of DNA polymerase I to fill in the gaps, it was blunt-end ligated into the BamHI site of pSM150. The complete gene cassette was excised as a single fragment with EcoR1 and HindIII and ligated into the same EcoR1 and HindIII sites of binary shuttle vector pBIN19. The new plasmid carrying the Kanamycin marker gene was designated as pSM151 and is shown in FIG. 4.

CONSTRUCTION OF pSM152

Figure 2:
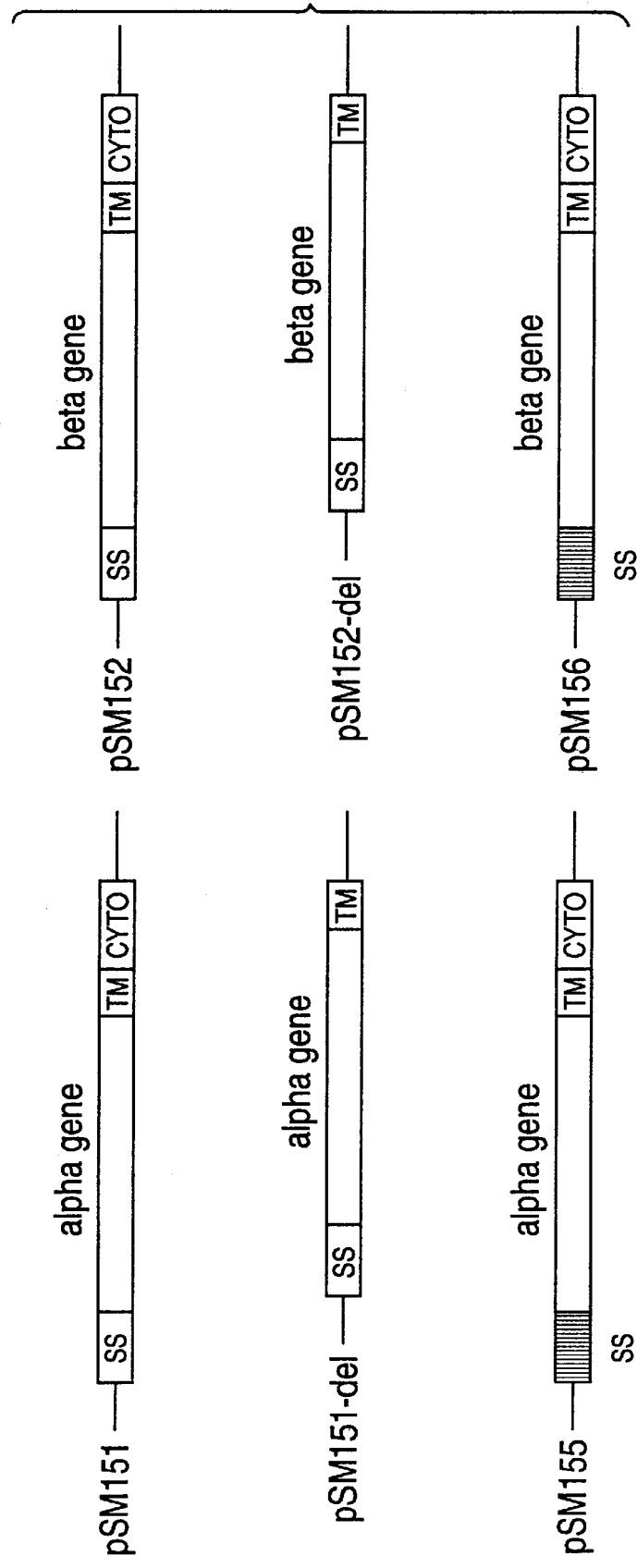
FIG. 2 shows a schematic diagram of some of the MHC class II α or β gene constructs of the invention in plant expression vectors.

The full length cDNA sequence for mouse class II MHC I-A $\beta$ gene subunit was obtained from Dr. Laurie Glimcher; it remained as a single EcoR1 fragment of about 900 bps. To insert I-A $\beta$ gene into pSM150, this EcoR1 fragment was gel-purified, filled in with klenow fragment, and blunt-end ligated. The complete gene cassette was then excised as a single fragment with EcoRI and HindIII and recloned into PBIN19, as for pSM151, to give pSM152 (FIG. 2).

All constructs were checked by sequencing to ensure the integrity of the MHC gene following manipulation.

EXAMPLE 2

Murine MHC II $\alpha$ chain and $\beta$ chain cDNAs were modified to remove the native leader peptide sequences and replace them with a plant-specific signal peptide sequence, as in FIG. 1. A DNA sequence coding for the signal peptide of barley $\alpha$ amylase was obtained from Dr. John C. Rogers, Department of Biology, Washington University.

CONSTRUCTION OF pSM155

The signal sequence was isolated from barley $\alpha$-amylase cDNA clone as a PCR product using two synthetic primers. The forward primer (5'-CGGATCCGGCGCGCGCCATGGGGAAG-3') (SEQ ID NO: 1) had a BamHI site added to 5' end to facilitate cloning, and the reverse primer (5'-GGAATTCCCGGGCGCCGGACGCCAAACCCGGC GAG-3') (SEQ ID NO: 2) contained two engineered restriction sites, EcoR1 and NarI. EcoR1 was used for convenience in subcloning whereas Nar1 provided a site for fusion. The PCR product was isolated, digested with BamHI and EcoR1, and cloned into pBluscriptII (Stratagene, an E. coli plasmid vector which does not have any NarI site), to form intermediate plasmid pBluscriptII-10.

The DNA fragment encoding the mature peptide sequence (native protein minus signal peptide) of murine II $\alpha$ chain was created by PCR using the following two synthetic primers: 5' GGGCGCCGAAGACGACATTGAGGCCGAC-3' (SEQ ID NO: 3) (forward reaction), which contained a compatible NarI site at its 5', and 5'-CGAATTCTCATAAAGGCCCTGGGTGTCT-3' (SEQ ID NO: 4) (reverse reaction) which had an EcoR1 site attached to the 5' end. The PCR product was rescued as an EcoR1+NarI fragment.

The rescued EcoR1+NarI fragment was ligated into pBluscriptII-10 which had previously been linearized by digestion with EcoR1 and NarI. The cDNA fragment containing chimeric $\alpha$ gene sequence was then excised with BamHI and EcoRV and subcloned into pSM150 at BamHI and SmaI sites. The complete expression cassette was further released following digestion with HindIII and EcoR1 and recloned into pBIN19 to give pSM155 (FIG. 2).

CONSTRUCTION OF pSM156 pSM156 was constructed by replacing the native signal sequence of I-A $\beta$ gene with the signal sequence of barley a-amylase (FIG. 2). The strategy employed was essentially the same as for the construction of pSM155. Two primers were used for the isolation of mature $\beta$ gene coding sequence:
5'-GGGCGCCGAAGACGACATTGAGGCCGAC-3' (SEQ ID NO: 5) (forward primer) and 5' CGAATTCTCATAAAGGCCCTGGGTGTCT-3' (SEQ ID NO: 6) (reverse primer).

EXAMPLE 3

CONSTRUCTION OF pSM151-del pSM151-del contains the truncated form of I-A $\alpha$ gene in which its DNA sequence determining the C-terminal cytoplasmic domain, was deleted, as in FIG. 1. This was obtained by polymerase chain reaction-mediated amplification after a 1.1 kb EcoR1 fragment was cloned into pUC19. The M13/PUC universal primer (5'-GTAAAACGACGGCCAGT-3') (SEQ ID NO: 7) is used as a forward primer. The reverse primer (5'-CGAATTCTCACAGGCCTTGAATGATGAAGAT-3') (SEQ ID NO: 8) corresponding to I-A $\alpha$ encoding sequence between nucleotides 715 and 732, introduces a termination codon TGA starting at nucleotide position 733, followed by an EcoR1 cloning site. The truncated gene was amplified by 25 cycles of heating (94° C., 1 min), annealing (55° C., 1.5 min), and extension (72° C., 2 min). The reaction product was purified, digested with EcoR1, blunt-ended with Klenow fragment, and first inserted into pSM150, and then the whole expression cassette was reisolated as a EcoR1 and HindIII fragment and subcloned into pBIN19 to give pSM151-del (FIG. 2).

CONSTRUCTION OF pSM152-del pSMA152-del contains the truncated I-A β gene which has its DNA sequence determining the C-terminal cytoplasmic domain removed (FIG. 2). This was accomplished essentially by the same procedure as used to construct PSM151-del. The M13/pUC universal primer was used as a forward primer. The reverse primer (5'-CGAATTCTCAGATGAAAAGGCCAAGCCCGAG-3') (SEQ ID NO: 9) which is complementary to the nucleotide sequence of I-A β gene at positions 715 and 735, introduced a TGA stop codon after nucleotide 715, followed by the same EcoR1 cloning site.

EXAMPLE 4

CONSTRUCTION of pSMA331 pSMA331 was derived from the Agrobacterium tumefaciens binary plasmid vector pBI4104. The complete NPTII-GUS gene expression cassette was removed and replaced with a 62 bp polylinker from M13 tq131. The resulting plasmid was designated as pSMA315. An expression cassette containing 35S-dual enhancer promoter and 3'-NOS terminator was cloned into the EcoR1-HindIII sites of PSMA315 to form plasmid pSMA325. A 2.2 kb BamHI fragment representing hygromycin phosphotransfererase (hpt) gene was isolated from pGL2 (Zyprian et al, Plant Mol. Biol (1990) 15:245) and filled in with klenow enzyme of DNA polymerase I, and blunt-end ligated into the BamHI site of pSMA325. The available unique cloning sites include BamHI, SmaI, XmaI, and KpnI. In PSMA331, hygromycin gene is used as a marker gene for selection of plant transformants. pSMA331 contains a RK2 replication origin and mobilization helper function. The construction of plasmid pSMA331 is shown in FIG. 5.

DNA sequences for murine class II MHC I-A α gene subunit (as in Example 1), chimeric αgene sequence (as in Example 2) and truncated α gene sequence (as in Example 3) were inserted into pSMA331 to give plasmids pSMA331-1, pSMA331-1-del and pSMA331-155 respectively, as shown in FIG. 5.

EXAMPLE 5

α-chain:—plasmids pSM151, pSM151-del and pSM155, which contained different forms of MHC II α chain gene, were individually mobilized into *Agrobacterium tumefaciens* strain LBA4404 by triparental plasmid transfer method (Ditta et al., (1980), Proc. Natl. Acad. Sci., vol. 77, pp. 7347–7351), and the exconjugants were used for transformation of tobacco, *Nicotiana tabacum*, cultivar SR1, by the leaf disk method. (Horsch et al., (1985), Science, vol. 227, pp. 1229–1231). Regeneration of transformed leaf disk into new plants was according to Horsch et al.

Primary screening of transformants was based on callus formation on MSO media supplemented with kanamycin.

β-chain:—the mobilization of plasmids pSM152, pSM152-del and pSM156, which contained different forms of MHCII β chain gene, into Agrobacterium and the transformation of tobacco SR1 were as described for the α chain gene.

Tobacco plants were also sequentially transformed with two *Agrobacterium tumefaciens* strains, containing an α chain gene and a hygromycin marker gene and a β chain gene and a kanamycin marker gene respectively. Plasmid pairs used included: pSM152 β chain and pSMA331-1 (full length Aαk gene cloned in pSMA331), pSM152-del and pSMA331-1-del (same as pSM151 except for vector used), and pSM156 β chain chimeric and pSMA331–155 (same as pSM155 except for vector used). Primary screening of transformants was based on the formation of callus on MSO media supplemented with both kanamycin and hygromycin.

A vector has been constructed containing both the α chain gene and the β chain gene of mouse MHC class II protein, each gene being inserted between an Ehn-35S promoter and a NOS-ter termination sequence, the two cassettes being sequential in the plasmid. This vector has been introduced into tobacco plants as described and transgenic plants have been obtained.

EXAMPLE 6

Regenerated tobacco plants transformed with either the full length α chain gene or the full length β chain gene (under control of the Ehn-35S promoter and with NOS-ter termination sequence) were examined for the presence of intact copy of MHC II α or β chain gene by Southern blotting. Total plant genomic DNA was extracted from 2.0 to 2.5 gm leaf tissue by standard methods, as described in Draper et al. (1988), "Plant Genetic Transformation and Gene Expression: A laboratory manual", Blackwell, Oxford. DNA fragments were separated on agarose gel after digestion with either EcoR1 and EcoR1 and HindIII, transferred to nylon membrane and probed with $^{32}p$ labelled DNA probes specific for either α chain gene or β chain gene, by Southern blot technique as described in Sambrook et al., (1989), "Molecular Cloning: A laboratory manual", 2nd Ed., Cold Spring Harbour Lab. Press, N.Y.

In the plants transformed with full-length α chain gene, when digested with EcoR1 and HindIII, a single hybridization band was found at the predicted size of 1.8 kb, indicating that the α chain gene was integrated into the plant nuclear genome as an intact DNA sequence (FIG. 6). Control non-transgenic plants showed no hybridization signal. When transformed plants were digested with EcoR1 alone, a single band was found at approximately 4.5 to 5.0 kb, indicating that only single copies of the DNAs were incorporated (data not shown). Similar results were obtained from β chain transgenic plants (FIG. 7) which also demonstrated single copy insertion.

Northern blot analysis as described in Sambrook (supra) was performed on total RNA extracts of leaf tissue from the transgenic plants and showed the stable accumulation of transgene mRNA transcripts of α chain (FIG. 8) and β chain (FIG. 9).

Western blot analysis as described by Sambrook (supra) was also carried out. Proteins were extracted by conventional methods from 2.0 to 2.5 gm leaf tissue from full length α chain or β chain transformants. 30 μg portions of protein were separated on 12% SDS—PAGE gel and gels were probed with antibodies against α or β chain polypeptide, revealing the presence of a unique protein band of the appropriate expected size as shown in FIGS. 10 and 11 respectively.

EXAMPLE 7

GAD in Tobacco

Full length cDNA coding for mouse GAD65 was obtained from Dr. B. Singh, University of Western Ontario.

A plasmid expression vector, pSM215, was constructed as shown in FIG. 12. A NcoI restriction site as indicated in Panel A was created by site-directed mutagenesis and used as part of a translational start site. Site-directed mutagenesis was done using the reaction kit purchased from Pharmacia following manufacturer's instructions. The primer used was 5'-GACCACCGAGCCATGGCATCTTC-3' (SEQ ID NO: 10) which includes a new NcoI restriction site. The modified murine DNA was cloned into plasmid pSM150. The translation start (ATG) and stop (TGA) sites are indicated. This GAD cDNA was inserted between the cauliflower mosaic virus 35S promoter, Ehn 35S, and the transcription termination sequence of nopaline synthase (NOS-ter).

The vector was transferred to tobacco plants by agrobacterium-mediated transformation as described in Examples 4 and 5. Transformed plants were selected by screening with kanamycin.

RNA was extracted from leaf tissue of transformants and subjected to Northern blot analysis, (25 μg RNA/lane, probed with $^{32}$P-GAD cDNA). Many transformants showed strong bands at the 2 kb size predicted for GAD65 mRNA as shown in FIG. 13.

Extracts of total protein from leaf tissue of transformed plants was subjected to Western blot analysis (30 μg protein/lane) using anti-mouse GAD antibody as probe. As seen in FIG. 14, many transformants showed a unique polypeptide of approximately 64 kDa, identical in size to the control band obtained using purified mouse GAD (Lane P: 100 ng protein). No similar band was observed in untransformed control plants (Lane C).

Tissue printing localisation of expressed GAD protein in intact transgenic tobacco leaves was carried out by the method of Cassab and Varner (1987) J. Cell Biol., 105, p. 2581. Leaves of both transgenic and untransformed tobacco plants were surface-blotted onto membranes and the prints were reacted with mouse anti-mouse GAD antibody followed by a rabbit anti-mouse antibody coupled to horse-radish peroxidase. The reaction signal was detected by an ECL (chemoluminescent) kit from Boehringer Mannheim. As seen in FIG. 15, the plant-produced mammalian protein GAD65 is distributed throughout the leaf tissue of the transgenic plant in a generally uniform fashion. Using scanning densitometry of the GAD bands obtained on Western blots of transformed leaf extracts, compared with standards comprising known quantities of mouse GAD, the production of mouse GAD protein in the transformed tobacco leaves was estimated to comprise 0.4% of total soluble proteins in the transformed leaf tissue.

EXAMPLE 8

Human GAD Expression in Potatoes

Two cDNA clones encoding portions of human GAD were used, representing either the 5' sequence or the 3' sequence. The two clones had an overlap sequence of no more than 70 nt. The complete human GAD sequence was made by a series of DNA manipulations. The N-terminal end of human GAD was modified by PCR to include the incorporation of a NcoI (CCATGG) restriction site as part of a translation initiation site. The native 3' nontranslated sequence, including poly A tail, was completely removed. The modified human GAD sequence was cloned into plasmid vector pTRL-GUS to replace the GUS gene. The plasmid pTRL GU3 is composed of CaMV 35S promoter with double enhancer sequence (Ehn-35S) linked to 5' untranslated TEV leader sequence, GUS gene and NOS-terminator. The new expression cassette, consisting of 5'-Ehn35S-TEV5' untranslated leader human GAD-NOS terminator was excised with HindIII and inserted into the binary vector pBIN19. The final construct, designated pSM215, was transferred into agrobacterium and potato transformation was carried out by the leaf disc method as described for tobacco transformation in Example 5.

The present invention is not limited to the features of the embodiments described herein, but includes all variations and modifications within the scope of the claims.

We claim:

1. A method for suppressing or reducing the immune response of a mammal to glutamic acid decarboxylase (GAD) comprising orally or enterally administering to the mammal an effective immunosuppressive dose of a plant tissue or a partially purified plant tissue extract containing GAD, said plant tissue or partially purified plant tissue extract being obtained from a transgenic plant expressing GAD.

2. The method of claim 1 wherein the transgenic plant is selected from the group consisting of potato, tomato, alfalfa, canola and tobacco.

3. The method of claim 1 wherein the plant tissue or partially purified plant tissue extract is selected from the group consisting of at least one plant part, an extract of total plant protein, and a partially purified plant protein preparation.

4. The method of claim 1 wherein the plant tissue or partially purified plant tissue extract is at least one plant part selected from the group consisting of leaves, stems, seeds and tubers.

5. The method of claim 1 wherein the transgenic plant is transformed with a DNA construct for transforming a plant, said construct comprising a Cauliflower Mosaic Virus Ehn-35S promoter operably linked to a DNA coding sequence and further comprising a termination sequence in proper reading frame with the DNA coding sequence, wherein the termination sequence is a nopaline synthase termination sequence and the DNA coding sequence encodes GAD.

6. The method of claim 1 wherein the mammal is a human.

7. The method of claim 6 wherein GAD is involved in the pathogenesis of autoimmune diabetes.

8. A pharmaceutical composition for suppressing or reducing the immune response of a mammal to GAD comprising an oral or enteral dosage form comprising an effective immunosuppressive dose of a plant tissue or partially purified plant tissue extract containing GAD and a pharmaceutically acceptable carrier, said plant tissue or partially purified plant tissue extract being obtained from a transgenic plant expressing GAD.

9. A transgenic plant expressing GAD.

10. The transgenic plant of claim 9 wherein the plant is an edible plant.

11. The transgenic plant of claim 9 wherein the plant is selected from the group consisting of potato, tomato, alfalfa, canola and tobacco.

12. An edible plant material comprising a plant tissue or partially purified plant tissue extract obtained from a transgenetic plant of claim 9.

13. An edible plant material comprising a plant tissue or partially purified plant tissue extract containing GAD, said plant tissue or partially purified plant tissue extract being obtained from a transgenic plant expressing GAD.

14. A transgenic plant wherein the plant is transfected with a DNA construct comprising a Cauliflower Mosaic Virus Ehn-35S promoter operably linked to a DNA coding sequence and further comprising a termination sequence in proper reading frame with the DNA coding sequence, wherein the termination sequence is a nopaline synthase termination sequence and the DNA coding sequence encodes GAD.

15. A method for suppressing or reducing the immune response of a mammal to GAD comprising orally or enterally administering to the mammal an effective immunosuppressive dose of a plant tissue or partially purified plant tissue extract containing an immunosuppressive fragment of GAD, said plan tissue or partially purified plant tissue extract being obtained from a transgenic plant expressing said immunosuppressive fragment of GAD.

16. The method of claim 15 wherein the mammal is a human.

17. A pharmaceutical composition for suppressing or reducing the immune response of a mammal to GAD comprising an oral or enteral dosage form comprising an effective immunosuppressive dose of a plant tissue or partially purified plant tissue extract containing an immunosuppressive fragment of GAD and a pharmaceutically acceptable carrier, said plant tissue or partially purified plant tissue extract being obtained from a transgenic plant expressing said immunosuppressive fragment of GAD.

\* \* \* \* \*

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "DNA - primer"

(xi) SEQUENCE DESCRIPTION: SEQ ID NO:1:

CGGATCCGGC GCGCGCCATG GGAAG                                     25

(2) INFORMATION FOR SEQ ID NO:2:

(i) SEQUENCE CHARACTERISTICS:
      (A) LENGTH: 35 base pairs
      (B) TYPE: nucleic acid
      (C) STRANDEDNESS: single
      (D) TOPOLOGY: linear (ii) MOLECULE TYPE: other nucleic acid (A) DESCRIPTION: /desc = "DNA - primer"

(xi) SEQUENCE DESCRIPTION: SEQ ID NO:2:

GGAATTCCCG GGCGCCGGAC GCCAAACCCG GCGAG                                    35

(2) INFORMATION FOR SEQ ID NO:3:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA - primer"

(xi) SEQUENCE DESCRIPTION: SEQ ID NO:3:

GGGCGCCGAA GACGACATTG AGGCCGAC                                            28

(2) INFORMATION FOR SEQ ID NO:4:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA - primer"

(xi) SEQUENCE DESCRIPTION: SEQ ID NO:4:

CGAATTCTCA TAAAGGCCCT GGGTGTCT                                            28

(2) INFORMATION FOR SEQ ID NO:5:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA - primer"

(xi) SEQUENCE DESCRIPTION: SEQ ID NO:5:

GGGCGCCGAA GACGACATTG AGGCCGAC                                            28

(2) INFORMATION FOR SEQ ID NO:6:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA - primer"

(xi) SEQUENCE DESCRIPTION: SEQ ID NO:6:

CGAATTCTCA TAAAGGCCCT GGGTGTCT                                            28

(2) INFORMATION FOR SEQ ID NO:7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear

```
        (ii) MOLECULE TYPE: other nucleic acid
             (A) DESCRIPTION: /desc = "DNA - primer"

(xi) SEQUENCE DESCRIPTION: SEQ ID NO:7:

GTAAAACGAC GGCCAGT                                                          17

(2) INFORMATION FOR SEQ ID NO:8:

(i) SEQUENCE CHARACTERISTICS:
             (A) LENGTH: 31 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "DNA - primer"

(xi) SEQUENCE DESCRIPTION: SEQ ID NO:8:

CGAATTCTCA CAGGCCTTGA ATGATGAAGA T                                          31

(2) INFORMATION FOR SEQ ID NO:9:

(i) SEQUENCE CHARACTERISTICS:
             (A) LENGTH: 31 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "DNA - primer"

(xi) SEQUENCE DESCRIPTION: SEQ ID NO:9:

CGAATTCTCA GATGAAAAGG CCAAGCCCGA G                                          31

(2) INFORMATION FOR SEQ ID NO:10:

(i) SEQUENCE CHARACTERISTICS:
             (A) LENGTH: 23 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "DNA - primer"

(xi) SEQUENCE DESCRIPTION: SEQ ID NO:10:

GACCACCGAG CCATGGCATC TTC                                                   23
```